US00PP10156P

United States Patent [19]

Roberson

[11] Patent Number: Plant 10,156

[45] Date of Patent: Dec. 23, 1997

[54] LANTANA PLANT NAMED 'ROBPATDES'

[76] Inventor: Robert J. Roberson, 31706 E. Pink Hill Rd., Grain Valley, Jackson County, Mo. 64029

[21] Appl. No.: 674,597

[22] Filed: Jun. 28, 1996

[51] Int. Cl.[6] ..... A01H 5/00

[52] U.S. Cl. ..... Plt./54.1

[58] Field of Search ..... Plt./54.1

*Primary Examiner*—James R. Feyrer
*Assistant Examiner*—Kent L. Bell
*Attorney, Agent, or Firm*—Rothwell, Figg, Ernst & Kurz

[57] ABSTRACT

A new cultivar of Lantana is provided, characterized particularly as to novelty by the growth vigor, the rapid woody trunk, the intensity of bloom color pigment, the dramatic multi-colored bloom display, and the very lush and deep green foliage.

1 Drawing Sheet

SUMMARY OF THE INVENTION

The invention relates to a new and distinct *Lantana camara* cultivar which is outstanding because of its growth vigor, its rapid woody trunk, its intensity of color pigment, its dramatic multi-colored bloom display, its very lush and deep green foliage, and was primarily selected for these characteristics. This selection was made from a specially designed Lantana hybridizing program with said hybrid cultivars being planted and grown in Grain Valley, Mo.

ORIGIN AND ASEXUAL REPRODUCTION

Asexual reproduction of this cultivar by tip cuttings was directed by me, such reproduction establishing that the plant does in fact maintain the characteristics described, in successive generations.

It should be noted that the plant was initially selected from a Lantana planting being grown near Grain Valley, Mo. in a cultivated area and has since been reproduced by tip cuttings in the vicinity of Grain Valley, Mo. with the new and distinct characteristics stated herein, found to be maintained through successive generations as before recited.

*Lantana camara* is native to the subtropics and tropical North and South America. They are woody ornamentals which are not winter hardy North of USDA horticulture Zone 9. The roughish leaves range from yellow-green to green to blue-green and the two basic growth forms are mounding and trailing (weeping). Bloom color usually includes yellow, white, cream, pink, or orange.

The cultivar of *Lantana camara* 'Robpatdes' may further be described as having a number of distinctive characteristics which are enumerated in the succeeding specific description but broadly stated as comprising a vigorous growth habit, a strong tendency to establish rapidly as a woody shrub and is excellent to produce a "tree standard" form with a multi-colored bloom display which transitions from orange/gold (PMS #115) to tones of old rose (PMS #184). The continuous color display begins blooming at 4–5 weeks after cuttings are made, or 3 weeks after potting. I have chosen to identify this new cultivar as *Lantana Camara* 'Robpatdes'. It is possible that other identification will be adopted in the trade, but the name selected will serve for the purposes hereof.

BRIEF DESCRIPTION OF THE DRAWING

The accompanying photograph shows as nearly true as it is reasonably possible to make the same, in color illustrations of this character, typical flowers of the new variety. The photographic drawing illustrates the flower form and the distinctive color transitions of the florets.

DETAILED DESCRIPTION

Figure 1:
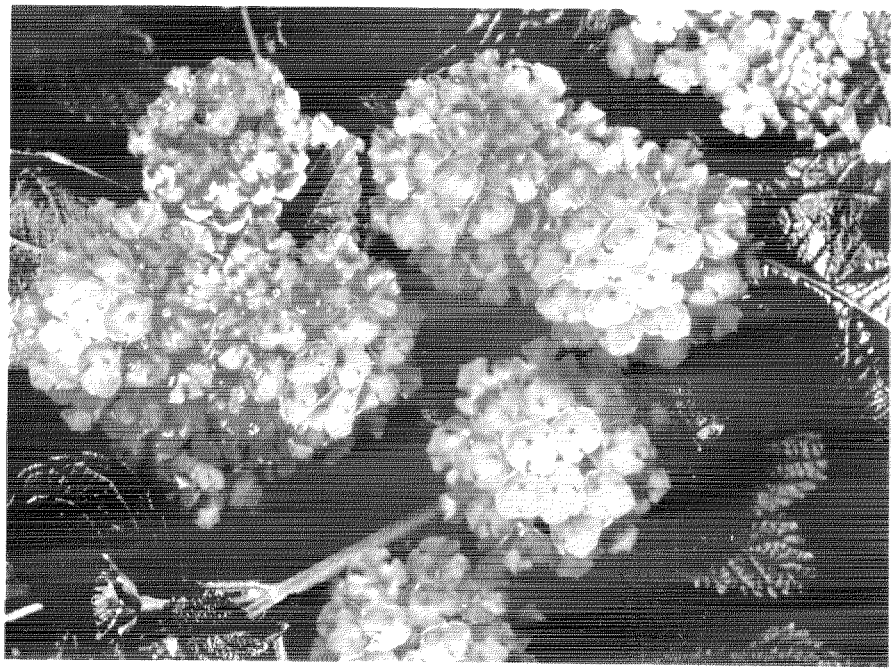
FIG. 1 illustrates the bloom cluster with varying maturity of the florets (to display the color range as well as possible).

In order to more specifically identify the cultivar, descriptive details are set forth hereinafter, along with related aspects of the plant which serve to distinguish the same, all colors being noted as compared with the Pantone Matching System (PMS). The measurements and colors were recorded from mature plants grown in the vicinity of Grain Valley, Mo.

Parentage:

*Seed parent.*—*Lantana camara* 'Firewagon' (in controlled open pollination).

*Pollen parent.*—Unknown.

Propagation: Asexual reproduction by tip cuttings started near Grain Valley, Mo.

Plant Descriptions

Inflorescence and reproductive parts: The inflorescence is a flat topped round cluster of 25–33 florets. The individual clusters are determinate and arise from the leaf axils. Each individual floret is slightly un-symmetrical with a bilateral symmetry and is subtended by a single bract. The perianth consist of: the Calyx (5 united petals) and the Corolla (5 united petals with narrow tube). The flowers are zygomorphic, hermaphroditic, and have 4 introse stamens which are didynamous.

The ovary is superior, the style is terminal, and the stigma is lobed. The ovary is 2 locular, but is divided into 4 loculi by a false septum in each loculus. The placentation is axile with 2 ovules per carpel.

The fruit classification is drupe and potentially contains 2 seeds. When fruit forms, it is green (PMS #363); then matures through a deep purple (PMS #533) to a near black (PMS #532).

Inflorescence:

*Dimensions.*—Bloom cluster — 1.5" in diameter. Single Floret — 0.4". Pedicle length — 1.4". Corolla tube — 0.5".

*Colors.*—Buds — Cream (PMS #127). First opening — Orange (PMS #136). Transitions through — Gold/orange (PMS #152 to PMS #158). Maturity — Fuschia (PMS #184). Tube — Lavender-pink in all stages (PMS #204).

Developmental pattern: First flowers develop in a circular pattern on the periphery of the inflorescence.

Leaves and stems:

*Leaf shape.*—Ovate.

*Leaf magins.*—Serrate.

*Leaf tip and base.*—Acute.

*Leaf veins.*—Pinnate.

*Leaf surface.*—Rough due to bristly hairs.

*Leaf arrangement.*—Opposite.

*Leaf color.*—Immature leaves — deep green (PMS #363) maturing to a slightly darker forest green (PMS #364).

*Leaf size.*—Length 3.8".

*Petiole.*—0.7".

*Width.*—1.9".

*Stem.*—Square in youth becoming round and woody with age.

Roots: Highly branched and fibrous.

Flowering time: The color display begins blooming at 6–7 weeks after cuttings are made, or 4 weeks after potting, and continue until temperatures drop below 45 degrees Fahrenheit.

Diseases: No unusual susceptibility to diseases noted to date.

Insects: Typical of this plant genius, white flies can be attracted to Lantana. There are no other insect problems known at this time.

General Observations

For the purpose of ornamental horticulture in our present living environments which include patio and balcony gardening, as well as open landscapes, *Lantana camara* plant 'Robpatdes' is ideal due to the following several characteristics:

A. Depth of color: The intensity of the yellow, gold, orange, fuschia shade is significantly more intense than other lantanas with this large woody growth habit.

B. Robust growth: 1. Due to its rapid and full growth habit, this cultivar is ideal for quickly establishing a color summer hedge, i.e., approximately 36" by the end of the annual growing season. 2. For the nursery grower this Lantana will make a nice saleable "standard", i.e., 3' trained tree form specialty product in one year. 3. The 30% larger than most Lantana leaves, give this cultivated variety a tropical foliage appearance which is unique and distinctive.

Comparison to Known Varieties

*Lantana camara* plant 'Robpatdes' should be compared with *Lantana camara* 'Lady Olivia' as this is the best color comparison of a Lantana with this larger woody growth habit known in today's trade. The inflorescence form and color presentations are similar. *Lantana camara* plant 'Robpatdes' is a vast improvement of the 'Lady Olivia' type due to the following:

A. The woody trunks of 'Robpatdes' is larger and stronger.

B. The internode spacing of the branches are closer, giving a more dense pattern overall.

C. The leaf color is a richer, darker green.

D. The bloom color display is much more intense in color pigment.

E. The blooms are more numerous and therefore the ratio of bloom-to-leaf on 'Robpatdes' is remarkably better (50% to 75% more blooms at any point in the summer season) than that of the comparison.

I claim:

1. A new and distinct cultivar of *Lantana camara* plant, substantially as described herein, characterized particularly as to novelty by the growth vigor, the rapid woody trunk, the intensity of bloom color pigment, the dramatic multi-colored bloom display, and the very lush and deep green foliage.

* * * * *